US007879820B2

(12) United States Patent
Müller

(10) Patent No.: US 7,879,820 B2
(45) Date of Patent: Feb. 1, 2011

(54) USE OF A CYCLODEXTRIN AS PEARLESCENT AGENT AND PEARLESCENT COMPOSITIONS

(75) Inventor: Rainer Müller, Leopoldshafen (DE)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 10/419,957

(22) Filed: Apr. 22, 2003

(65) Prior Publication Data

US 2004/0033984 A1    Feb. 19, 2004

Related U.S. Application Data

(60) Provisional application No. 60/377,593, filed on May 6, 2002.

(30) Foreign Application Priority Data

Apr. 22, 2002    (FR) ................................. 02 05004

(51) Int. Cl.
*A61K 31/715*    (2006.01)
*A61K 31/695*    (2006.01)
(52) U.S. Cl. .......................................... 514/58; 514/63
(58) Field of Classification Search .................... 514/58, 514/63
See application file for complete search history.

(56) References Cited

U.S. PATENT DOCUMENTS

| | | | |
|---|---|---|---|
| 2,528,378 A | 10/1950 | Mannheimer | |
| 2,781,354 A | 2/1957 | Mannheimer | |
| 4,678,598 A | 7/1987 | Ogino et al. | |
| 4,693,935 A | 9/1987 | Mazurek | |
| 4,719,099 A | 1/1988 | Grollier et al. | |
| 4,728,571 A | 3/1988 | Clemens et al. | |
| 4,839,166 A | 6/1989 | Grollier et al. | |
| 4,972,037 A | 11/1990 | Garbe et al. | |
| 5,139,037 A | 8/1992 | Grollier et al. | |
| 5,196,189 A | 3/1993 | Jacquet et al. | |
| 5,275,755 A | 1/1994 | Sebag et al. | |
| 5,618,523 A | 4/1997 | Zysman et al. | |
| 5,718,905 A * | 2/1998 | Skiba et al. ............... | 424/499 |
| 5,958,392 A | 9/1999 | Grollier et al. | |
| 6,025,510 A | 2/2000 | Wimmer et al. | |
| 6,153,219 A * | 11/2000 | Creeth et al. ............... | 424/451 |
| 2002/0077265 A1 * | 6/2002 | Buzzacarini et al. ........ | 510/296 |

FOREIGN PATENT DOCUMENTS

| | | |
|---|---|---|
| DE | 44 02 929 | 6/1995 |
| DE | 44 20 736 | 8/1995 |
| DE | 44 24 530 | 1/1996 |
| DE | 44 24 533 | 1/1996 |
| EP | 0 186 507 | 7/1986 |
| EP | 0 227 994 | 7/1987 |
| EP | 0 246 090 | 11/1987 |
| EP | 0 337 354 | 10/1989 |
| EP | 0 342 834 | 11/1989 |
| EP | 0 412 704 | 2/1991 |
| EP | 0 412 707 | 2/1991 |
| EP | 0 582 152 | 2/1994 |
| EP | 0 646 572 | 4/1995 |
| EP | 1 046 390 | 10/2000 |
| JP | 62 267218 | 11/1987 |
| JP | 62 267220 | 11/1987 |
| JP | 3 172397 | 7/1991 |
| JP | H6-126814 | 5/1994 |
| JP | 8 310925 | 11/1996 |
| JP | 2000/230078 | 8/2000 |
| WO | WO 93/23009 | 11/1993 |
| WO | WO 93/23446 | 11/1993 |
| WO | WO 94/07844 | 4/1994 |
| WO | WO 94/10131 | 5/1994 |
| WO | WO 94/24097 | 10/1994 |
| WO | WO 95/00578 | 1/1995 |
| WO | WO 95/16665 | 6/1995 |
| WO | WO 95/23807 | 9/1995 |
| WO | WO 98/03155 | 1/1998 |

OTHER PUBLICATIONS

Patent Abstracts of Japan, vol. 016, No. 283 (C-0955), Jun. 24, 1992, JP 04 074107.
Patent Abstracts of Japan, vol. 011, No. 024 (C-399), Jan. 23, 1987, JP 61 197509.
Hans-Jürgen Buschmann et al., "Applications of cyclodextrins in cosmetic products: A review", J. Cosmet. Sci., vol. 53, May/Jun. 2002, pp. 185-191.
M.R. Porter. BSc, PhD, CChem, MRSC, "Handbook of Surfactants," Blackie & Son Ltd., 1991, pp. 116-178.
Todd et al., "Volatile Silicone Fluids for Cosmetic Formulations", Cosmetics & Toiletries, vol. 91, Jan. 1976, pp. 29-32.

* cited by examiner

*Primary Examiner*—Shaojia Anna Jiang
*Assistant Examiner*—Everett White
(74) *Attorney, Agent, or Firm*—Finnegan, Henderson, Farabow, Garrett & Dunner, L.L.P.

(57) ABSTRACT

Use of at least one agent chosen from cyclodextrins and the derivatives thereof as a pearlescent agent, in a composition, for example, a pearlescent cosmetic composition, comprising a physiologically acceptable aqueous medium. Use of at least one agent chosen from cyclodextrins and the derivatives thereof and at least one surfactant in compositions. Pearlescent compositions comprising, a physiologically acceptable aqueous medium, at least one agent chosen from cyclodextrins and the derivatives thereof, at least one surfactant, and at least one conditioning agent; as well as use of at least one agent chosen from cyclodextrins and the derivatives thereof as an agent for suspending an insoluble conditioning agent; wherein the compositions disclosed herein may be used in a form chosen, for example, from rinse-out products, for example, for washing and/or conditioning a keratinous material.

28 Claims, No Drawings

USE OF A CYCLODEXTRIN AS PEARLESCENT AGENT AND PEARLESCENT COMPOSITIONS

This application claims benefit of U.S. Provisional Application No. 60/377,593, filed May 6, 2002.

Disclosed herein is the use of at least one agent chosen from cyclodextrins and the derivatives thereof as a pearlescent agent, in a composition, for example, a cosmetic composition, comprising, in a physiologically acceptable aqueous medium, at least one surfactant. Also disclosed herein are pearlescent compositions comprising, in a physiologically acceptable aqueous medium, at least one agent chosen from cyclodextrins and the derivatives thereof and at least one surfactant; further disclosed herein are pearlescent compositions comprising, in a physiologically acceptable aqueous medium, at least one agent chosen from cyclodextrins and the derivatives thereof, at least one surfactant, and at least one conditioning agent. Also disclosed herein is the use of at least one agent chosen from cyclodextrins and the derivatives thereof for suspending an insoluble conditioning agent.

As used herein, the term "pearling agent" or "pearlescent agent" means an agent producing at least one of pearlescent, iridescent, shimmering and metallic appearances and effects.

It is well-known that hair which has been sensitized (i.e. damaged and/or embrittled) to various degrees under the action of atmospheric agents or under the action of mechanical or chemical treatments, such as dyeing, bleaching and/or permanent waving, may often be difficult to disentangle and to style, and may lack softness.

The use of conditioning agents, for example, insoluble conditioning agents that can facilitate the disentanglement of hair and can make hair soft, shiny and supple has already been recommended in compositions for washing or care of a keratinous material such as hair.

Given the insoluble character of certain conditioning agents such as silicones and oils, it is sought to be able to maintain the conditioning agents in a uniform dispersion in the medium without, however, causing a drop in the viscosity, and the detergent and foaming properties of the compositions. The conditioning agents, such as silicones and oils, can also be carried to the treated keratinous materials and may confer on them, following the application, at least one property of softness, sheen and disentanglement.

It is also well-known that products, for example, cosmetic products, having an iridescent, shimmering or metallic appearance or effect are widely appreciated by consumers for their esthetic appearance which can give an appearance of richness to the product. The agents which can provide this effect are pearling agents which may be in the form of crystals which can remain dispersed in the compositions and which can reflect light.

Long-chain ester derivatives are widely used for pearling compositions, for example, pearling cosmetic compositions. However, these derivatives can exhibit problems of crystallization which may cause a variation in the viscosity of the compositions over time.

Long-chain ether or thioether derivatives such as those described in Patent Application Nos. EP457688 and WO98/03155 are also known. However, they can opacify the compositions and may not give or not sufficiently give the compositions pearliness.

To obtain the pearlescent effect, the compositions comprising the pearlescent agents can be heated to above the melting point of the pearlescent agents and then cooled in order to cause them to crystallize.

It has been observed that these pearlescent agents, because of their low density, may have the disadvantage of rising to the surface of a shampoo and may form, as a result, a layer on the surface which can be inesthetic to the consumer.

Furthermore, these fatty chain compounds may have, in some cases, the disadvantages of giving a charged feel to the hair, and a lack of lightness and volume of the hair.

A need therefore still exists for novel pearlescent agents which may not exhibit at least one of the disadvantages mentioned above and which may also allow the use of constituents such as insoluble conditioning agents, for example, silicones.

The inventor has discovered, surprisingly, that it was possible to formulate compositions, such as cosmetic compositions, for the treatment of a keratinous material, for example, shampoos having a pearlescent appearance while having at least one of the desired esthetic and cosmetic properties, comprising, in these compositions, at least one agent chosen from cyclodextrins and the derivatives thereof and, for example, at least one surfactant.

The inventor has discovered that the use of at least one agent chosen from cyclodextrins and the derivatives thereof may make it possible to pearl and/or enhance pearling of compositions, for example, cosmetic compositions, comprising at least one surfactant.

The pearlescence obtained may be very shiny. Moreover, the preparation of the compositions may be carried out in the cold state, which can be very advantageous.

Furthermore, the at least one agent chosen from cyclodextrins and the derivatives thereof may make it possible to maintain in suspension conditioning agents which are insoluble in water and/or the composition. The at least one agent chosen from cyclodextrins and the derivatives thereof may also make it possible to stabilize the viscosity of the composition according to the temperature, i.e., it may reduce the variation in the viscosity with the temperature.

Disclosed herein is the use of at least one agent chosen from cyclodextrins and the derivatives thereof as a novel pearlescent and/or opacifying agent. Further disclosed herein is the use of at least one agent chosen from cyclodextrins and the derivatives thereof as a novel pearlescent and/or opacifying agent in a cosmetic composition, for example, a washing and/or conditioning composition, comprising a physiologically acceptable aqueous medium and at least one surfactant.

Also disclosed herein are pearlescent compositions, for example, pearlescent cosmetic compositions, comprising, in an aqueous medium, for example, a physiologically acceptable aqueous medium, at least one surfactant and at least one agent chosen from cyclodextrins and the derivatives thereof, wherein the at least one agent chosen from cyclodextrins and the derivatives thereof and the at least one surfactant are present at effective concentrations to pearl the compositions.

Further disclosed herein are pearlescent compositions, for example, pearlescent cosmetic compositions, comprising, in an aqueous medium, for example, a physiologically acceptable aqueous medium, at least one surfactant and at least one agent chosen from cyclodextrins and the derivatives thereof, wherein the at least one agent chosen from cyclodextrins and the derivatives thereof and the at least one surfactant are present at effective concentrations to form an insoluble complex in the compositions.

The compositions disclosed herein may at least satisfactorily exhibit at least one of following properties: homogeneity, stability of the pearlescence, and a viscosity for application to a keratinous material.

Other embodiments will appear upon reading the description and the examples disclosed herein.

The cyclodextrins disclosed herein may, for example, be chosen from oligosaccharides of formula (I):

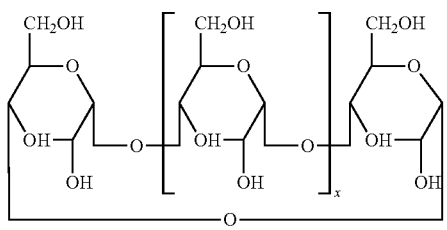

wherein:
x may be a number equal to 4 (which corresponds to α-cyclodextrin), to 5 (β-cyclodextrin) or to 6 (γ-cyclodextrin).

It may be possible, for example, to use a beta-cyclodextrin sold by the company WACKER under the name CAVAMAX W7 and a gamma-cyclodextrin sold by the company WACKER under the name CAVAMAX W8.

The cyclodextrin derivatives may, for example, be chosen from methylcyclodextrins such as the methyl-beta-cyclodextrin marketed by the company WACKER under the name CAVASOL W7.

The at least one agent chosen from cyclodextrins and the derivatives thereof may be present in an amount ranging, for example, from 0.2% to 30% by weight, further, for example, from 1% to 15% by weight, and still further, for example, from 1.5% to 10% by weight, of the total weight of the composition.

The compositions disclosed herein may, for example, further comprise at least one surfactant in an amount ranging, for example, from 0.2% to 40% by weight, further, for example, from 1% to 35% and still further, for example, from 1.5% to 30% by weight, relative to the total weight of the composition.

The at least one agent chosen from cyclodextrins and the derivatives thereof and the at least one surfactant may, for example, be present at concentrations which are effective for pearling the composition and/or for forming an insoluble complex in the composition, for example, between the at least one agent chosen from cyclodextrins and the derivatives thereof and the at least one surfactant.

When the at least one surfactant is present, the at least one surfactant/at least one agent ratio may range, for example, from 0.01:1 to 300:1, further, for example, from 0.1:1 to 100:1 and, even further, for example, from 0.3:1 to 25:1.

The at least one surfactant suitable for use in the compositions disclosed herein may be of any type, and for example, may be soluble in water at room temperature, chosen, for example, from:

(i) Anionic Surfactants:

The nature of the anionic surfactants is not of truly critical importance within the context of the embodiments disclosed herein.

Thus, the anionic surfactants that may be employed, in the compositions disclosed herein, may be chosen, for example, from at least one of salts, for example, alkali metal salts such as sodium salts; ammonium salts; amine salts; amino alcohol salts; and magnesium salts; of the following compounds: alkyl sulfates, alkyl ether sulfates, alkylamido ether sulfates, alkylaryl-polyether sulfates, monoglyceride sulfates, alkyl sulfonates, alkyl phosphates, alkylamido sulfonates, alkyl aryl sulfonates, α-olefinsulfonates, paraffin-sulfonates, alkyl sulfosuccinates, alkyl ether sulfosuccinates, alkylamidesulfosuccinates, alkyl sulfosuccinamates, alkyl sulfoacetates, alkyl ether phosphates, acyl sarcosinates, acyl isethionates and N-acyltaurates, and the alkyl and acyl radicals of all these different compounds, for example, comprising from 8 to 24 carbon atoms, and the aryl radicals, for example, being chosen from phenyl and benzyl groups.

The anionic surfactants may also be chosen, for example, from at least one of the salts of fatty acids such as the salts of oleic, ricinoleic, palmitic and stearic acids and the salts of the acids of copra oil and of hydrogenated copra oil. The anionic surfactants may also be chosen, for example, from at least one of acyl lactylates wherein the acyl radical comprises from 8 to 20 carbon atoms.

It may also be possible to employ weakly anionic surfactants chosen from, for example, at least one of alkyl-D-galactosideuronic acids, polyoxyalkylenated carboxylic ($C_6$-$C_{24}$) alkyl ether acids, polyoxyalkylenated carboxylic ($C_6$-$C_{24}$) alkylaryl ether acids, polyoxyalkylenated carboxylic ($C_6$-$C_{24}$)alkyl amidoether acids and the salts thereof, for example, those comprising from 2 to 50 ethylene oxide groups.

The anionic surfactants may further, for example, be chosen from at least one of the salts of alkyl sulfates and of alkyl ether sulfates.

(ii) Nonionic Surfactants:

The nonionic surfactants themselves are also compounds which are well known per se (in this respect see, for example, the "Handbook of Surfactants" by M. R. Porter, published by Blackie & Son (Glasgow and London), 1991, pp. 116-178) and, in the context of the embodiments disclosed herein, their nature is not of critical importance. Thus, the nonionic surfactants can be chosen, (nonlimiting list), for example, from at least one of alcohols, such as alpha-diols and alkylphenols; polyethoxylated fatty acids; polypropoxylated fatty acids; and polyglycerolated fatty acids, comprising at least one fatty chain comprising, for example, from 8 to 18 carbon atoms, it being possible for the number of ethylene oxide groups or propylene oxide groups to range, for example, from 2 to 50 and it being possible for the number of glycerol groups to range, for example, from 2 to 30. The nonionic surfactants may also be chosen, for example, from at least one of copolymers of ethylene oxides and propylene oxides; condensates of ethylene oxides and propylene oxides with fatty alcohols can also be used in the compositions disclosed herein; polyethoxylated fatty amides comprising, for example, from 2 to 30 mol of ethylene oxides; polyglycerolated fatty amides comprising, for example, from 1 to 5 glycerol groups, and further, for example, from 1.5 to 4 glycerol groups; polyethoxylated fatty amine comprising, for example, from 2 to 30 mol of ethylene oxides; oxyethylenated fatty acid esters of sorbitan comprising, for example, from 2 to 30 mol of ethylene oxides; fatty acid esters of sucrose; fatty acid esters of polyethylene glycol; alkylpolyglycosides; N-alkylglucamine derivatives; and amine oxides such as the oxides of ($C_{10}$-$C_{14}$) alkylamines and the N-acylaminopropylmorpholine oxides can also be used.

The nonionic surfactants may be chosen, for example, from alkylpoly-glycosides for use in the compositions disclosed herein.

(iii) Amphoteric or Zwitterionic Surfactants:

The amphoteric or zwitterionic surfactants, the nature of which is not of critical importance in the embodiments disclosed herein, may be chosen (nonlimiting list), for example, from at least one of derivatives of aliphatic secondary and tertiary amines, wherein the aliphatic radical may be chosen from linear and branched chains comprising from 8 to 18 carbon atoms and comprising at least one water-solubilizing anionic group chosen, for example, from carboxylate, sulfonate, sulfate, phosphate and phosphonate groups; ($C_8$-$C_{20}$) alkylbetaines, sulfobetaines, ($C_8$-$C_{20}$)alkylamido($C_1$-$C_6$) alkylbetaines and ($C_8$-$C_{20}$)alkylamido($C_1$-$C_6$) alkylsulfobetaines.

The amine derivatives may be chosen, for example, from products sold under the name MIRANOL, as described in U.S. Pat. Nos. 2,528,378 and 2,781,354 and classified in the CTFA dictionary, 3rd edition, 1982, under the names Amphocarboxyglycinates and Amphocarboxypropionates and having the respective structures (II) and (III):

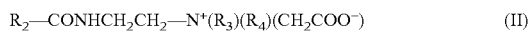

$$R_2\text{—CONHCH}_2\text{CH}_2\text{—N}^+(R_3)(R_4)(\text{CH}_2\text{COO}^-) \qquad (II)$$

wherein:

$R_2$ is chosen from alkyl radicals derived from acids $R_2$—COOH present in hydrolyzed copra oil; a heptyl radical; a nonyl radical; and a undecyl radical, $R_3$ is chosen from beta-hydroxyethyl groups, and $R_4$ is chosen from carboxymethyl groups; and

$$R_{2'}\text{—CONHCH}_2\text{CH}_2\text{—N(B)(C)} \qquad (III)$$

wherein:

B is chosen from —$CH_2CH_2OX'$ groups,

C is chosen from —$(CH_2)_z$—Y' groups, wherein z=1 or 2, and

X' is chosen from a —$CH_2CH_2$—COOH group and a hydrogen atom,

Y' is chosen from a —COOH group and the radical —$CH_2$—CHOH—$SO_3H$, and $R_{2'}$ is chosen from alkyl radicals derived from acids $R_{2'}$—COOH present in copra oil; alkyl radicals derived from acids $R_{2'}$—COOH present in hydrolyzed linseed oil; alkyl radicals, such as $C_7$, $C_9$, $C_{11}$, and $C_{13}$ alkyl radicals; and saturated and unsaturated $C_{17}$ alkyl radicals and its iso forms. For example, the amphoteric or zwitterionic surfactants may be cocoamphodiacetate marketed under the trade name MIRANOL C2M concentrate NP by the company RHODIA CHIMIE.

(iv) Cationic Surfactants:

The cationic surfactants may be chosen, for example, from:

A) quaternary ammonium salts of the following general formula (IV):

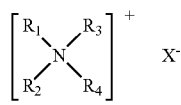

wherein:

$X^-$ is an anion chosen from halides, such as chloride, bromide and iodide; ($C_2$-$C_6$)alkyl sulfates, such as methyl sulfate, phosphates; alkyl and alkylaryl sulfonates; and anions derived from organic acids such as acetate and lactate, and (i) the radicals $R_1$ to $R_3$, which may be identical or different, are each chosen from linear and branched aliphatic radicals comprising from 1 to 4 carbon atoms, and aromatic radicals such as aryl and alkylaryl radicals. The aliphatic radicals may comprise at least one heteroatom chosen, for example, from oxygen, nitrogen, sulfur, and halogens. The aliphatic radicals may, for example, be chosen from alkyl, alkoxy and alkylamide radicals.

$R_4$ is chosen from linear and branched alkyl radicals comprising from 16 to 30 carbon atoms.

For example, the cationic surfactants may be chosen from salts, such as chloride, of cetyltrimethylammonium.

ii) the radicals $R_1$ and $R_2$, which may be identical or different, are each chosen from linear and branched aliphatic radicals comprising from 1 to 4 carbon atoms and aromatic radicals such as aryl and alkylaryl. The aliphatic radicals may comprise at least one heteroatom chosen, for example, from oxygen, nitrogen, sulfur, and halogens. The aliphatic radicals may, for example, be chosen from alkyl, alkoxy, alkylamide and hydroxyalkyl radicals comprising from 1 to 4 carbon atoms;

$R_3$ and $R_4$, which may be identical or different, are each chosen from linear and branched alkyl radicals comprising from 12 to 30 carbon atoms, wherein said alkyl radicals comprise at least one group chosen from ester groups and amide functional groups, $R_3$ and $R_4$, which may be identical or different, can, for example, each be chosen from radicals ($C_{12}$-$C_{22}$)alkylamido ($C_2$-$C_6$)alkyl and ($C_{12}$-$C_{22}$)alkyl acetate.

For example, the cationic surfactants may be chosen from salts such as chloride of stearamidopropyld imethyl(myristylacetate)ammonium.

B) quaternary ammonium salts of imidazolinium, for example, salts of the following formula (V):

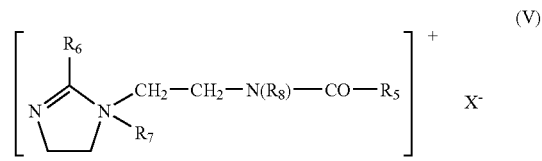

wherein:

$R_5$ is chosen from alkenyl and alkyl radicals comprising from 8 to 30 carbon atoms, for example, alkyl radicals derived from tallow fatty acids, $R_6$ is chosen from a hydrogen atom, $C_1$-$C_4$ alkyl radicals and alkenyl and alkyl radicals comprising from 8 to 30 carbon atoms, $R_7$ is chosen from $C_1$-$C_4$ alkyl radicals, $R_8$ is chosen from a hydrogen atom and $C_1$-$C_4$ alkyl radicals, $X^-$ is an anion chosen from halides, phosphates, acetates, lactates, alkyl sulfates, alkyl and alkylaryl sulfonates.

For example, $R_5$ and $R_6$, which may be identical or different, can each be chosen from mixtures of alkenyl and alkyl radicals comprising from 12 to 21 carbon atoms, for example, alkyl radicals derived from tallow fatty acids; $R_7$ can be a methyl radical, and $R_8$ can be a hydrogen. Such a product is, for example, Quaternium-27 (CTFA 1997) or Quaternium-83 (CTFA 1997) marketed under the names "REWOQUAT" W 75, W90, W75PG, W75HPG by the company WITCO.

C) quaternary diammonium salts of formula (VI):

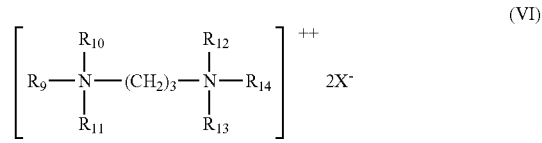

wherein:

$R_9$ is chosen from aliphatic radicals comprising from 16 to 30 carbon atoms, $R_{10}$, $R_{11}$, $R_{12}$, $R_{13}$, $R_{14}$, which may be identical or different, are each chosen from hydrogen and alkyl radicals comprising from 1 to 4 carbon atoms, and $X^-$ is an anion chosen from halides, acetates, phosphates, nitrates and methyl sulfates. Such quaternary diammonium salts may, for example, be propane tallow diammonium dichloride.

D) quaternary ammonium salts comprising at least one ester functional group of the following formula (VII):

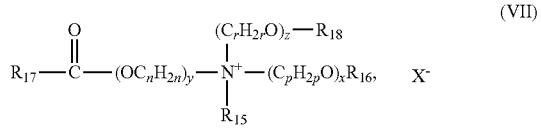

wherein:

$R_{15}$ is chosen from $C_1$-$C_6$ alkyl radicals and $C_1$-$C_6$ hydroxyalkyl and dihydroxyalkyl radicals;

$R_{16}$ is chosen from:
the radical

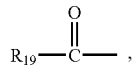

the radical $R_{20}$, wherein $R_{20}$ is chosen from saturated and unsaturated, linear and branched $C_1$-$C_{22}$ hydrocarbon radicals, and
a hydrogen atom;

$R_{18}$ is chosen from:
the radical

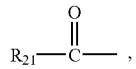

the radical $R_{22}$, wherein the radical $R_{22}$ is chosen from saturated and unsaturated, linear and branched $C_1$-$C_6$ hydrocarbon radicals, and
a hydrogen atom;

$R_{17}$, $R_{19}$, and $R_{21}$, which may be identical or different, are each chosen from saturated and unsaturated, linear and branched $C_7$-$C_{21}$, hydrocarbon radicals;

n, p and r, which may be identical or different, are each chosen from integers ranging from 2 to 6;

y is chosen from integers ranging from 1 to 10;

x and z, which may be identical or different, are each chosen from integers ranging from 0 to 10;

$X^-$ is an anion chosen from simple and complex, organic and inorganic anions;

provided that the sum of x+y+z is equal to an integer ranging from 1 to 15, that when x is equal to 0, then $R_{16}$ is $R_{20}$ and that when z is equal to 0 then $R_{18}$ is $R_{22}$.

For example, the ammonium salts of formula (IV) may be used, wherein:

$R_{15}$ is chosen from methyl and ethyl radicals;

x and y are equal to 1;

z is equal to 0 or 1;

n, p and r are equal to 2;

$R_{16}$ is chosen from:
the radical

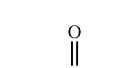

methyl, ethyl and $C_{14}$-$C_{22}$ hydrocarbon radicals, and
a hydrogen atom;

$R_{17}$, $R_{19}$ and $R_{21}$, which may be identical or different, are each chosen from saturated and unsaturated, linear and branched $C_7$-$C_{21}$ hydrocarbon radicals; and $R_{18}$ is chosen from:
the radical

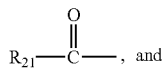

a hydrogen atom.

Such compounds are, for example, marketed under the names DEHYQUART by the company COGNIS, STEPANQUAT by the company STEPAN, NOXAMIUM by the company CECA, REWOQUAT WE 18 by the company REWO-WITCO.

The quaternary ammonium salts may, for example, be chosen from cetyltrimethylammonium chloride and palmitamidopropyltrimethylammonium chloride marketed under the name VARISOFT PA TC by the company GOLDSCHMIDT.

In one embodiment, at least one anionic surfactant chosen, for example, from sodium triethanolamine and ammonium ($C_{12}$-$C_{14}$) alkyl sulfates, sodium triethanolamine and ammonium ($C_{12}$-$C_{14}$)alkyl ether sulfates oxyethylenated with 2.2 mol of ethylene oxide, sodium cocoyl isethionate, and sodium alpha-($C_{14}$-$C_{16}$)Olefin sulfonates may be used with:

either at least one amphoteric surfactant chosen, for example, from the amine derivatives called disodium cocoamphodiacetate and sodium cocoamphopropionate marketed, for example, by the company RHODIA CHIMIE under the trade name "MIRANOL® C2M CONCNP" as an aqueous solution comprising 38% of active substance or marketed under the tradename MIRANOL® C32;

or at least one amphoteric surfactant chosen, for example, from alkylbetaines, for example, the cocobetaine marketed under the name "DEHYTON® AB 30" as an aqueous solution comprising 32% AS by the company COGNIS or such as the ($C_8$-$C_{20}$)alkylamido($C_1$-$C_6$) alkylbetaines, for example, the TEGOBETAINE® F 50 marketed by the company GOLDSCHMIDT.

The relative concentrations of the surfactants in the composition disclosed herein may be as follows:

the at least one anionic surfactant (i) may be present in an amount ranging, for example, from 2 to 50% by weight, and further, for example, from 3 to 20% by weight, relative to the total weight of the composition;

the at least one nonionic surfactant (ii) may be present in an amount ranging, for example, from 1 to 30% by weight, and further, for example, from 1 to 15% by weight, relative to the total weight of the composition;

the at least one amphoteric or zwitterionic surfactant (iii) may be present in an amount ranging, for example, from 1 to 30% by weight, and further, for example, from 1 to 15% by weight, relative to the total weight of the composition.

According to one embodiment disclosed herein, the cosmetic compositions may also comprise at least one conditioning agent for conditioning a keratinous material.

Disclosed herein, therefore, are also pearlescent cosmetic compositions, for example, washing and/or conditioning compositions, comprising, in a physiologically acceptable aqueous medium, at least one surfactant, at least one conditioning agent, and at least one agent chosen from cyclodextrins and the derivatives thereof.

These compositions, when applied to the hair, may possess good hair conditioning properties, i.e., the treated hair may possess at least one of the following properties: smooth, easy to disentangle, and soft feel. As a result, the hair may have a natural look and may not appear lank.

The compositions disclosed herein comprising at least one conditioning agent may be stable: for example, the at least one conditioning agent may not be released or uncontrolled thickening of the composition may not occur over time. Finally, the compositions disclosed herein can have a non-runny and fondant texture. The foam formed can be rinsed out easily.

Also disclosed herein is a method of washing and/or conditioning using the compositions disclosed herein.

Further disclosed herein is the use of at least one agent chosen from cyclodextrins and the derivatives thereof as an agent for suspending at least one conditioning agent which is insoluble in a cosmetic composition, for example, a washing and/or conditioning composition, comprising a physiologically acceptable aqueous medium and at least one surfactant.

The at least one conditioning agent may be maintained in suspension by the complex formed, for example, between the at least one surfactant and the at least one agent chosen from cyclodextrins and the derivatives thereof and may not be complexed with the at least one agent.

When the compositions disclosed herein comprise at least one conditioning agent, the at least one conditioning agent may, for example, be chosen from synthetic oils, for example, polyolefins such as poly-α-olefins, fluorinated oils, fluorinated waxes, fluorinated gums, carboxylic acid esters, cationic polymers, silicones, mineral, plant and animal oils, ceramides and pseudoceramides.

The polyolefins may be chosen, for example, from poly-α-olefins, such as:
  hydrogenated and non-hydrogenated polybutene type poly-α-olefins, for example, hydrogenated and non-hydrogenated polyisobutenes. Isobutylene oligomers with a molecular weight of less than 1000 and mixtures thereof with polyisobutylenes with a molecular weight of greater than 1000, for example, polyisobutylenes with a molecular weight ranging from 1000 to 15000 may, for example, be used.
  For example, the poly-α-olefins which can be used in the compositions disclosed herein, may be chosen from polyisobutenes sold under the name PERMETHYL 99 A, 101 A, 102 A, 104 A (n=16) and 106 A (n=38) by the company PRESPERSE Inc., and the products sold under the name Arlamol HD (n=3) by the company ICI (n denoting the degree of polymerization).
  and hydrogenated and non-hydrogenated polydecene type poly-α-olefins.

Such products are sold, for example, under the names Ethylflo by the company Ethyl Corp. and Arlamol PAO by the company ICI.

The mineral oils which may be used in the compositions disclosed herein may, for example, be chosen from hydrocarbons, such as hexadecane and liquid petroleum jelly.

The vegetable oils may be chosen, for example, from sweet almond oil, avocado oil, castor oil, olive oil, jojoba wax, sunflower oil, wheat germ oil, sesame oil, peanut oil, grapeseed oil, soybean oil, rapeseed oil, safflower oil, copra oil, corn oil, hazelnut oil, shea butter, palm oil, apricot stone oil, and calophyllum oil. The vegetable oil may also, for example, be chosen from transesterified vegetable oils, for example, olive oil transesterified with hexanol, and jojoba wax transesterified with ethanol.

The cationic polymers which may be used in the compositions disclosed herein may be chosen from any of those already known per se as improving the cosmetic properties of hair treated with detergent compositions, such as those described in Patent Application No. EP-A-0 337 354 and in French Patent Application Nos. FR-A-2 270 846, 2 383 660, 2 598 611, 2 470 596 and 2 519 863.

As used herein, the expression "cationic polymer" means any polymer comprising at least one group chosen from cationic groups and groups which may be ionized into cationic groups.

The cationic polymers which can be used in the compositions disclosed herein, may be chosen, for example, from quaternary cellulose ether derivatives such as the products sold under the name "JR400" by the company Union Carbide Corporation, cyclopolymers, for example, homopolymers of a diallyldimethylammonium salt and copolymers of a diallyldimethylammonium salt and of acrylamide, for example, the chlorides, sold under the names "Merquat 100", "Merquat 550" and "Merquat S" by the company Merck, cationic polysaccharides and further, for example, guar gums modified with 2,3-epoxypropyltrimethylammonium chloride sold, for example, under the name "Jaguar C13S" by the company Meyhall, optionally crosslinked homopolymers and copolymers of a (meth)acryloyloxyethyltrimethylammonium salt, sold by the company Allied Colloids as a 50% solution in mineral oil, under the trade names Salcare SC92 (crosslinked copolymer of methacryloyloxyethyltrimethylammonium chloride and of acrylamide) and Salcare SC95 (crosslinked homopolymer of methacryloyloxyethyltrimethylammonium chloride).

It may also be possible to use the polymers which comprise repeating units corresponding to the formula (VII):

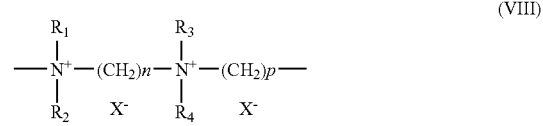

(VIII)

wherein:

$R_1$, $R_2$, $R_3$ and $R_4$, which may be identical or different, are each chosen from alkyl and hydroxyalkyl radicals comprising from 1 to 4 carbon atoms, n and p, which may be identical or different, are each integers ranging from 2 to 20, and $X^-$ is an anion chosen from anions derived from acids chosen from inorganic and organic acids.

The silicones which can be used in the compositions disclosed herein may, for example, be chosen from polyorganosiloxanes which are insoluble in the composition and may be in the form chosen from oils, waxes, resins, and gums.

The water-insoluble silicones are insoluble in water at a concentration of greater than or equal to 0.1% by weight in water at 25° C., i.e., they do not form a transparent isotropic solution.

The viscosity of the silicones is measured, for example, at 25° C. according to ASTM standard 445 Appendix C.

The polyorganosiloxanes are defined, for example, in greater detail in the book by Walter NOLL "Chemistry and Technology of Silicones" (1968) Academie Press. They may be chosen from volatile and nonvolatile polyorganosiloxanes.

When they are chosen from volatile polyorganosiloxanes, the silicones may, for example, be chosen from those volatile polyorganosiloxanes having a boiling point ranging from 60° C. to 260° C., and further, for example, may be chosen from:

(i) at least one of cyclic silicones comprising, for example, from 3 to 7 silicon atoms, for example, from 4 to 5 silicon atoms. They may, for example, be chosen from octamethylcyclotetrasiloxane marketed, for example, under the name "VOLATILE SILICONE 7207" by UNION CARBIDE and "SILBIONE 70045 V 2" by RHODIA CHIMIE, and decamethylcyclopentasiloxane marketed under the name "VOLATILE SILICONE 7158" by UNION CARBIDE, "SILBIONE 70045 V 5" by RHODIA CHIMIE and mixtures thereof.

The cyclic silicones may also be chosen from cyclocopolymers of the dimethylsiloxane/methylalkylsiloxane type, such as the "SILICONE VOLATILE FZ 3109" marketed by the company UNION CARBIDE, having the chemical structure:

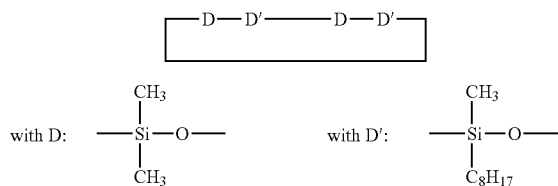

The cyclic silicones may also be chosen, for example, from mixtures of cyclic silicones with organic compounds derived from silicon, such as the mixture of octamethylcyclotetrasiloxane and tetratrimethylsilylpentaerythritol (50/50) and the mixture of octamethylcyclotetrasiloxane and 1,1'-oxy(2,2,2', 2',3,3'-trimethylsilyloxy)bisneopentane;

(ii) linear volatile silicones comprising from 2 to 9 silicon atoms and having a viscosity of less than or equal to $5 \times 10^{-6}$ m$^2$/s at 25° C. For example, decamethyltetrasiloxane marketed, for example, under the name "SH 200" by the company TORAY SILICONE can be used. Silicones chosen from this class are also described in the article published in Cosmetics and Toiletries, Vol. 91, January 76, p. 27-32—TODD & BYERS "Volatile Silicone fluids for cosmetics".

The nonvolatile silicones may, for example, be chosen from at least one of polyalkylsiloxanes, polyarylsiloxanes, polyalkylarylsiloxanes, silicone gums and resins, and polyorganosiloxanes modified by organofunctional groups. These nonvolatile silicones may, for example, be chosen from polyalkylsiloxanes. The polyalkylsiloxanes may be chosen, for example, from polydimethylsiloxanes with terminal trimethylsilyl groups having a viscosity ranging from $5 \times 10^{-6}$ to 2.5 m$^2$/s at 25° C., for example, ranging from $1 \times 10^{-5}$ to 1 m$^2$/s.

These polyalkylsiloxanes may also be chosen, for example, from the following commercial products:

oils of the MIRASIL series marketed by the company RHODIA CHIMIE, such as the MIRASIL DM 500 000 oil;
oils of the 200 series from the company DOW CORNING, for example, DC200 having a viscosity of 60 000 Cst; and
VISCASIL oils from GENERAL ELECTRIC and certain oils of the SF series (SF 96, SF 18) from GENERAL ELECTRIC.

The polyalkylsiloxanes may also, for example, be chosen from polydimethyl-siloxanes with terminal dimethylsilanol groups (Dimethiconol according to the CTFA name), such as the oils of the 48 series from the company RHODIA CHIMIE.

In this class of polyalkylsiloxanes, the polyalkylsiloxanes may further be chosen from the products marketed under the names "ABIL WAX 9800 and 9801" by the company GOLDSCHMIDT which are poly($C_1$-$C_{20}$)alkylsiloxanes.

The polyalkylarylesiloxanes may, for example, be chosen from polydimethyl methylphenylsiloxanes, linear and branched polydimethyl diphenylsiloxanes having a viscosity ranging from $1 \times 10^{-5}$ to $5 \times 10^{-2}$ m$^2$/s at 25° C.

These polyalkylarylsiloxanes may further be chosen, for example, from the products marketed under the following names:

MIRASIL DPDM oils from RHODIA CHIMIE;
oils of the RHODORSIL 70633 and 763 series from RHODIA CHIMIE;
DOW CORNING 556 COSMETIC GRAD FLUID oil from DOW CORNING;
silicones of the PK series from BAYER such as the product PK20;
silicones of the PN, PH series from BAYER such as the products PN1000 and PH1000; and
certain oils of the SF series from GENERAL ELECTRIC such as SF 1023, SF 1154, SF 1250, and SF 1265.

The silicone gums, which can be used in the compositions disclosed herein, may, for example, be chosen from polydiorganosiloxanes having high number-average molecular masses ranging from 200 000 to 1 000 000, used alone or as a mixture in a solvent. This solvent may be chosen, for example, from at least one of volatile silicones, polydimethylsiloxane (PDMS) oils, polyphenylmethylsiloxane (PPMS) oils, isoparaffins, polyisobutylenes, methylene chloride, pentane, dodecane, and tridecane.

The silicone gums may, for example, be chosen from:
polydimethylsiloxane,
polydimethylsiloxane/methylvinylsiloxane gums,
polydimethylsiloxane/diphenylsiloxane,
polydimethylsiloxane/phenylmethylsiloxane, and
polydimethylsiloxane/diphenylsiloxane/methylvinylsiloxane.

The silicone gums may further, for example, be chosen from the following mixtures:

the mixtures formed from a polydimethylsiloxane hydroxylated at the chain end (called dimethiconol according to the nomenclature of the CTFA dictionary) and from a cyclic dimethylsiloxane (called cyclomethicone according to the nomenclature of the CTFA dictionary) such as the product Q2 1401 marketed by the company DOW CORNING;
the mixtures formed from a polydimethylsiloxane gum with a cyclic silicone such as the product SF 1214 Silicone Fluid from the company GENERAL ELECTRIC; this product is a gum SF 30 corresponding to a dimethicone, having a number-average molecular weight of 500 000, solubilized in the oil SF 1202 Silicone Fluid corresponding to decamethylcyclopentasiloxane; and
the mixtures of two PDMSs of different viscosities, and, for example, of a PDMS gum and a PDMS oil, such as the product SF 1236 from the company GENERAL ELECTRIC. The product SF 1236 is the mixture of an SE 30 gum defined above having a viscosity of 20 m$^2$/s and an SF 96 oil having a viscosity of $5 \times 10^{-6}$ m$^2$/s. This product, for example, comprises 15% of SE 30 gum and 85% of an SF 96 oil.

The polyorganosiloxane resins, which can be used in the compositions disclosed herein may, for example, be chosen from crosslinked siloxane systems comprising the units: $(R)_2SiO_{2/2}$, $(R)_3SiO_{1/2}$, $RSiO_{3/2}$ and $SiO_{4/2}$ wherein R is hydrocarbon groups comprising from 1 to 16 carbon atoms and a phenyl group. For example, the polyorganosiloxane resins may be chosen from those resins wherein R is chosen from $C_1$-$C_4$ lower alkyl radicals, for example, a methyl radical, and a phenyl radical.

For example, these resins may be chosen from the product marketed under the name "DOW CORNING 593" and those marketed under the names "SILICONE FLUID SS 4230 and SS 4267" by the company GENERAL ELECTRIC and which are silicones having the dimethyl/trimethylsiloxane structure.

Further, for example, these resins may be chosen from the resins of the trimethylsilyloxysilicate type which are marketed, for example, under the names X22-4914, X21-5034 and X21-55037 by the company SHIN-ETSU.

The organomodified silicones, which can be used in the compositions disclosed herein may, for example, be chosen from the silicones defined above and comprising in their structure at least one organofunctional group attached via a hydrocarbon radical.

For example, the organomodified silicones may be chosen, for example, from the polyorganosiloxanes comprising at least one group chosen from:
  polyethyleneoxy and polypropyleneoxy groups optionally comprising at least one alkyl group chosen from $C_6$-$C_{24}$ alkyl groups such as the products called dimethicone-copolyol marketed by the company DOW CORNING under the name DC 1248 and the oils SILWET L 722, L 7500, L 77, L 711 from the company UNION CARBIDE and the ($C_{12}$)alkyl methicone-copolyol marketed by the company DOW CORNING under the name Q2 5200;
  substituted and unsubstituted amine-containing groups such as the products marketed under the name GP 4 Silicone Fluid and GP 7100 by the company GENESEE and the products marketed under the names Q2 8220 and DOW CORNING 929 and 939 by the company DOW CORNING. The substituted amine-containing groups may, for example, be chosen from $C_1$-$C_4$ aminoalkyl groups;
  thiol groups, such as the products marketed under the names "GP 72 A" and "GP 71" from GENESEE;
  alkoxylated groups, such as the product marketed under the name "SILICONE COPOLYMER F-755" by SWS SILICONES and ABIL WAX 2428, 2434 and 2440 by the company GOLDSCHMIDT;
  hydroxylated groups, such as the polyorganosiloxanes with a hydroxyalkyl functional group which are described in French Patent Application No. FR-A-85 16334.
  acyloxyalkyl groups such as the polyorganosiloxanes described in U.S. Pat. No. 4,957,732;
  anionic groups of the carboxylic type, such as the products described in Patent No. EP 186 507 from the company CHISSO CORPORATION, and anionic groups of the alkylcarboxylic type, such as those present in the product X-22-3701E from the company SHIN-ETSUU; 2-hydroxyalkylsulfonate; 2-hydroxyalkylthiosulfate such as the products marketed by the company GOLD-SCHMIDT under the names "ABIL S201" and "ABIL S255"; and
  hydroxyacylamino groups, such as the polyorganosiloxanes described in Patent Application No. EP 342 834, for example, the product Q2-8413 from the company DOW CORNING.

In one embodiment, it may also be possible to use silicones comprising a polysiloxane portion and a portion comprising a nonsilicone organic chain, wherein one of the two portions constitutes the principal chain of the polymer, the other is grafted onto said principal chain. These polymers are, for example, described in Patent Application Nos. EP-A-412 704, EP-A-412 707, EP-A-640 105 and WO 95/00578, EP-A-582 152 and WO 93/23009 and U.S. Pat. Nos. 4,693,935, 4,728,571 and 4,972,037. These polymers may, for example, be anionic or nonionic.

Such polymers may, for example, be the copolymers which can be obtained by free-radical polymerization starting with a mixture of monomers, comprising:
  a) 50 to 90% by weight of tert-butyl acrylate;
  b) 0 to 40% by weight of acrylic acid; and
  c) 5 to 40% by weight of silicone-containing macromer of formula:

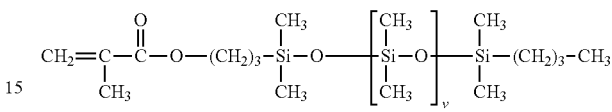

wherein:
  v is a number ranging from 5 to 700; the percentages by weight being calculated relative to the total weight of the monomers.

The graft silicone-containing polymers may, for example, be chosen from polydimethylsiloxanes (PDMS) on which are grafted, via a linking member of the thiopropylene type, mixed polymer units of the poly(meth)acrylic acid type and of the polyalkyl (meth)acrylate type, and polydimethylsiloxanes (PDMS) on which are grafted, via a linking member of the thiopropylene type, polymer units of the polyisobutyl (meth)acrylate type.

As used herein, all the silicones may, for example, be in a form of emulsions.

For example, the polyorganosiloxanes used in the compositions disclosed herein may be chosen, for example, from:
  nonvolatile silicones chosen from the family of polyalkylsiloxanes with trimethylsilyl terminal groups such as oils having a viscosity ranging from 0.2 to 2.5 m$^2$/s at 25° C. such as the oils of the DC200 series from DOW CORNING, for example, that of viscosity 60 000 Cst, of the MIRASIL DM series and further, for example, the oil MIRASIL DM 500 000 marketed by the company RHODIA CHIMIE and the silicone oil AK 300 000 from the company WACKER, the polyalkylsiloxanes with dimethylsilanol terminal groups such as dimethiconol and the polyalkylarylsiloxanes such as the MIRASIL DPDM oil marketed by the company RHODIA CHIMIE; and
  polysiloxanes with amino groups such as amodimethicones and trimethylsilylamodimethicones.

As disclosed herein, the compounds of the ceramide type may be chosen, for example, from natural and synthetic ceramides, glycoceramides, pseudoceramides and neoceramides.

The compounds of the ceramide type may be chosen from those described, for example, in Patent Application Nos. DE 4 424 530, DE 4 424 533, DE 4 402 929, DE 4 420 736, WO 95/23807, WO 94/07844, EP-A-0 646 572, WO 95/16665, FR-2 673 179, EP-A-0 227 994, WO 94/07844, WO 94/24097 and WO 94/10131.

The compounds of the ceramide type may, for example, be chosen from at least one of:
  2-N-linoleoylaminooctadecane-1,3-diol,
  2-N-oleoylaminooctadecane-1,3-diol,
  2-N-palmitoylaminooctadecane-1,3-diol,
  2-N-stearoylaminooctadecane-1,3-diol,
  2-N-behenoylaminooctadecane-1,3-diol,
  2-N-[2-hydroxypalmitoyl]aminooctadecane-1,3-diol,
  2-N-stearoylaminooctadecane-1,3,4-triol, for example, N-stearoyl-phytosphingosine,
  2-N-palmitoylaminohexadecane-1,3-diol,
  bis(N-hydroxyethyl-N-cetyl)malonamide, N-(2-hydroxyethyl)-N-(3-cetyloxy-2-hydroxypropyl) cetylamide, and N-docosanoyl-N-methyl-D-glucamine.

As disclosed herein, the at least one conditioning agent may be present in an amount ranging, for example, from 0.001% to 10% by weight, further, for example, from 0.005% to 5% by weight, and even further, for example, from 0.01% to 3% by weight, of the total weight of the composition.

The physiologically acceptable medium may be chosen, for example, from water and mixtures of water and at least one solvent chosen from cosmetically and dermatologically acceptable solvents such as monoalcohols, polyalcohols, glycol, and ethers. The water may, for example, be present in an amount ranging from 30 to 98% by weight, and for example, from 50 to 98% by weight, relative to the total weight of the composition.

For example, the at least one solvent may be chosen from lower alcohols. such as ethanol and isopropanol; polyalcohols such as diethylene glycol and glycerol; glycol ethers; and alkyl ethers of glycol and of diethylene glycol.

The compositions disclosed herein may also comprise at least one additive chosen from sequestering agents, softeners, foam modifiers, dyes, other pearlescent agents, moisturizing agents, antidandruff and antiseborrheic agents, other suspension agents, fatty acids comprising at least one chain chosen from linear and branched $C_{16}$-$C_{40}$ chains, hydroxy acids, electrolytes, thickeners, fatty acid esters, fragrances, preserving agents, sunscreens, proteins, vitamins and provitamins, polymers and any other additives conventionally used in cosmetics.

The at least one additive may be present in the compositions disclosed herein in an amount ranging from 0 to 40% by weight, relative to the total weight of the composition. The precise amount of each additive depends on its nature and is readily determined by a person skilled in the art.

Needless to say, a person skilled in the art will take care to select the optional compound(s) to be added to the compositions disclosed herein such that the advantageous properties intrinsically associated with the compositions disclosed herein are not, or are not substantially, adversely affected by the envisaged addition(s).

For example, to have a pearlescent effect, the at least one agent chosen from cyclodextrins and the derivatives thereof should generally not form a complex with the at least one conditioning agent and/or the at least one additive present in the composition.

The compositions disclosed herein may, for example, be in the form chosen from gels, milks, creams, more or less thickened lotions, and mousses.

The compositions disclosed herein may, for example, be used for treating a keratinous material chosen, for example, from hair, skin, eyelashes, eyebrows, nails, lips, and scalp, and, for example, the hair.

The compositions may also be used, for example, for washing and/or cleansing a keratinous material such as the hair and the skin.

The compositions disclosed herein may, for example, be used as products for, for example, washing, caring for, conditioning, maintaining the hairstyle, and/or for shaping a keratinous material such as the hair.

The compositions disclosed herein may further, for example, be provided in a form chosen from shampoos; rinse-out and leave-in conditioners; compositions for permanent-waving, straightening, dyeing, and bleaching; compositions to be applied before and after dyeing, bleaching, permanent-waving and straightening; and between the two steps of a permanent-waving and straightening operation. For example, the compositions disclosed herein may be provided in a form chosen from washing and foaming compositions for the hair and/or the skin.

In one embodiment, the compositions disclosed herein may be provided in a form chosen from foaming detergent compositions such as shampoos, shower gels and bubble baths. For example, the compositions can comprise at least one detergent surfactant.

The at least one detergent surfactant may be chosen from the anionic, amphoteric, nonionic, zwitterionic and cationic surfactants described above.

The minimum amount of the at least one detergent surfactant is that which is just sufficient to give the composition a satisfactory foaming power and/or detergent power.

Thus, as disclosed herein, the at least one detergent surfactant may be present in an amount ranging, for example, from 3% to 30% by weight, further, for example, from 6% to 25% by weight and even further, for example, from 8% to 20% by weight, relative to the total weight of the composition.

The foaming power of the compositions disclosed herein, measured by a foam height, may, for example, be greater than 75 mm and further, for example, greater than 100 mm, measured according to the modified Ross-Miles method (NF T 73-404/ISO 696).

The modifications to the method are as follows:

The measurement is performed at a temperature of 22° C. with osmosed water. The concentration of the solution is 2 g/l. The drop height is 1 m. The amount of a composition which is dropped is 200 ml. The 200 ml of the composition fall into a measuring cylinder 50 mm in diameter and comprising 50 ml of the test composition. The measurement is carried out 5 minutes after stopping the flow of the composition.

The compositions disclosed herein may also be in the form chosen from rinse-out and leave-in conditioners, compositions for permanent-waving, straightening, dyeing and bleaching; rinse-out compositions to be applied before and after dyeing, bleaching, permanent-waving and straightening; and between the two steps of a permanent-waving and straightening operation.

When the composition disclosed herein is provided in the form chosen from conditioners, optionally a rinse-out conditioner, it may also, for example, comprise at least one cationic surfactant, in an amount ranging, for example, from 0.1 to 10% by weight, further for example, from 0.5 to 5% by weight, relative to the total weight of the composition.

The compositions disclosed herein may also be provided, for example, in the form chosen from washing compositions for the skin, for example, in the form chosen from bath and shower solutions, gels and make-up-removing products.

The compositions disclosed herein may also be provided, for example, in the form chosen from aqueous and aqueous-alcoholic lotions for skin and/or hair care.

The cosmetic compositions disclosed herein may also be provided, for example, in the form chosen from gels, milks, creams, emulsions, thickened lotions, and mousses and may be used for a keratinous material chosen from the skin, the nails, the eyelashes, the lips, and the hair.

The compositions disclosed herein may be packaged in various forms. For example, it may be packaged in a form chosen from vaporizers, pump dispensers, and aerosol containers so as to allow application of the composition in vaporized form and in foam form. Such forms of packaging are recommended, for example, when it may be desired to obtain a spray, a lacquer or a foam for treating hair.

Also disclosed herein is a method for cosmetic treatment of a keratinous material such as hair, comprising applying to the keratinous material the composition disclosed herein and then optionally rinsing with water after a possible leave-in time.

The compositions disclosed herein may, for example, be prepared by mixing the at least one agent chosen from cyclodextrins and the derivatives thereof and the water of the composition and then adding the at least one surfactant. The embodiments disclosed herein will now be illustrated more fully with the aid of the following examples which cannot be considered as limiting the embodiments described. In the text which follows, as well as above, AS means Active Substance.

EXAMPLE 1

Three shampoos having the following compositions were prepared:

Compositions A and B were prepared according to the embodiments disclosed herein, composition C is a comparative composition, lacking the at least one agent chosen from cyclodextrins and the derivatives thereof as disclosed herein.

|  | A | B | C |
|---|---|---|---|
| sodium lauryl ether sulfate oxyethylenated with 2.2 mol of ethylene oxide as an aqueous solution containing 70% AS | 15.5 g AS | 15.5 g AS | 15.5 g AS |
| cocoylbetaine as an aqueous solution containing 30% AS | 2.9 g AS | 2.9 g AS | 2.9 g AS |
| beta-cyclodextrin (CAVAMAX W7 from WACKER | 2.5 g | | |
| gamma-cyclodextrin (CAVAMAX W8 from WACKER | | 2.5 g | |
| mixture of cetyl alcohol (50% by weight) and hydroxystearyl cetyl ether (50% by weight) | | | 2.5 g |
| dimethicone (MIRASIL DM 500000 from RHODIA CHIMIE | 2.7 g | 2.7 g | 2.7 g |
| guar gum modified with 2,3-epoxypropyl-trimethylammonium chloride (JAGUAR C13 S from RHODIA CHIMIE) | 0.05 g | 0.05 g | 0.05 g |
| carbomer (GARBOPOL 980 from NOVEON | 0.2 9 | 0.2 g | 0.2 g |
| sodium ketostearyl (50/50 by weight) sulfate | 0.75 g | 0.75 g | 0.75 g |
| propylene glycol | 0.1 g | 0.1 g | 0.1 g |
| preservatives, perfume | qs qs | qs | |
| NaOH qs | pH 6.5-7 | pH 6.5-7 | pH 6.5-7 |
| demineralized water qs | 100 g | 100 g | 100 g |

The quantity of water needed was placed in a tank, then the modified guar gum was added, then the sodium ketostearyl sulfate was added and then the carbomer was added.

After homogenizing, the cyclodextrin was introduced. Next, the sodium lauryl sulfate containing 2.2 mol of ethylene oxide and the betaine were added. After homogenizing, the dimethicone, optionally predispersed with a portion of the surfactants, was introduced. After forming the emulsion, the preservatives, the propylene glycol and the perfume were added and the pH was adjusted.

The compositions A and B made according to the present disclosure had a higher pearlescent white effect than that of composition C and, for example, had a very bright pearlescent effect by visual observation.

Hair washed with the composition A or B was less rough and had more volume than hair treated with the composition C.

EXAMPLE 2

Rinse-out conditioners having the following composition were prepared:

| In g AS | A | B | C | D |
|---|---|---|---|---|
| Cyclodextrin (Cavamax W 7 from WACKER) | 2.5 | 5 | 5 | — |
| Hydroxyethylcellulose | 1 | 1 | 1.5 | 1 |

-continued

| In g AS | A | B | C | D |
|---|---|---|---|---|
| PEG-7 glyceryl (CETIOL HE from COGNIS) | 0.5 | 0.5 | 0.5 | 0.5 |
| Palmitamidopropyl trimethylammonium chloride (VARISOFT PA TC from GOLDSCHMIDT) | 2.4 | 2.4 | 2.4 | 2.4 |
| pH | 3.6 | 3.3 | 3.7 | 3.3 |
| Perfume | qs | qs | qs | qs |
| Preservatives | qs | qs | qs | qs |
| Demineralized water | qs 100 g | qs 100 g | qs 100 g | qs 100 g |

Compositions A, B and C prepared according to the present disclosure were pearlescent gels. Composition D was a clear (transparent) gel.

What is claimed is:

1. A pearlescent composition comprising,
    an aqueous medium,
    at least one conditioning agent,
    at least one surfactant, and
    at least one agent chosen from unsubstituted β-cyclodextrins or methyl β-cyclodextrins,
    wherein the at least one surfactant and the at least one agent chosen from unsubstituted β-cyclodextrins or methyl β-cyclodextrins are present in sufficient concentrations to pearl the composition;
    wherein the at least one conditioning agent is chosen from poly-α-olefins, fluorinated oils, fluorinated waxes, fluorinated gums, carboxylic acid esters, silicons, cationic polymers, mineral oils, plant oils, animal oils, ceramides, and pseudoceramides; and
    wherein the at least one agent chosen from unsubstituted β-cyclodextrins or methyl β-cyclodextrins does not form a complex with the at least one conditioning agent.

2. The composition according to claim 1, wherein the at least one agent chosen from β-cyclodextrins is present in an amount ranging from 0.2% to 30% by weight, relative to the total weight of the composition.

3. The composition according to claim 2, wherein the at least one agent chosen from β-cyclodextrins is present in an amount ranging from 1% to 15% by weight, relative to the total weight of the composition.

4. The composition according to claim 1, wherein the at least one surfactant is present in an amount ranging from 0.2% to 40% by weight, relative to the total weight of the composition.

5. The composition according to claim 4, wherein the at least one surfactant is present in an amount ranging from 1% to 35% by weight, relative to the total weight of the composition.

6. The composition according to claim 1, wherein the at least one conditioning agent is present in an amount ranging from 0.001% to 10% by weight, relative to the total weight of the composition.

7. The composition according to claim 6, wherein the at least one conditioning agent is present in an amount ranging from 0.005% to 5% by weight, relative to the total weight of the composition.

8. The composition according to claim 7, wherein the at least one conditioning agent is present in an amount ranging from 0.01% to 3% by weight, relative to the total weight of the composition.

9. The composition according to claim 1, wherein the composition is chosen from gels, milks, creams, lotions, and mousses.

10. The composition according to claim 1, wherein the composition is a foaming detergent composition.

11. The composition according to claim 10, wherein the foaming detergent composition is chosen from shampoos, shower gels, and bubble baths.

12. The composition according to claim 1, wherein the composition is chosen from rinse-out and leave-in conditioner compositions; compositions for permanent-waving, straightening, dyeing and bleaching; compositions to be applied before dyeing, bleaching, permanent-waving and straightening; compositions to be applied after dyeing, bleaching, permanent-waving and straightening; and compositions to be applied between the two steps of a permanent-waving and straightening operation.

13. A pearlescent composition comprising,
    an aqueous medium,
    at least one conditioning agent, and
    at least one insoluble complex in said pearlescent composition, said at least one insoluble complex comprising at least one surfactant and at least one agent chosen from cyclodextrins,
    wherein the at least one conditioning agent is chosen from poly-α-olefins, fluorinated oils, fluorinated waxes, fluorinated gums, carboxylic acid esters, silicones, cationic polymers, mineral oils, plant oils, animal oils, ceramides, and pseudoceramides.

14. The composition according to claim 13, wherein, the at least one agent chosen from cyclodextrins is chosen from α-cyclodextrin, β-cyclodextrin, and γ-cyclodextrin.

15. The composition according to claim 14, wherein the at least one agent chosen from cyclodextrins is chosen from β-cyclodextrin and γ-cyclodextrin.

16. The composition according to claim 14, wherein the at least one agent chosen from cyclodextrins is chosen from methylcyclodextrins.

17. The composition according to claim 13, wherein the at least one agent chosen from cyclodextrins is present in an amount ranging from 0.2% to 30% by weight, relative to the total weight of the composition.

18. The composition according to claim 17, wherein the at least one agent chosen from cyclodextrins is present in an amount ranging from 1% to 15% by weight, relative to the total weight of the composition.

19. The composition according to claim 18, wherein the at least one surfactant is present in an amount ranging from 0.2% to 40% by weight, relative to the total weight of the composition.

20. The composition according to claim 19, wherein the at least one surfactant is present in an amount ranging from 1% to 35% by weight, relative to the total weight of the composition.

21. The composition according to claim 13, wherein the at least one conditioning agent is present in an amount ranging from 0.001% to 10% by weight, relative to the total weight of the composition.

22. The composition according to claim 21, wherein the at least one conditioning agent is present in an amount ranging from 0.005% to 5% by weight, relative to the total weight of the composition.

23. The composition according to claim 22, wherein the at least one conditioning agent is present in an amount ranging from 0.01% to 3% by weight, relative to the total weight of the composition.

24. The composition according to claim 13, wherein the composition is chosen from gels, milks, creams, lotions, and mousses.

25. The composition according to claim 13, wherein the composition is a foaming detergent composition.

26. The composition according to claim 25, wherein the foaming detergent composition is chosen from shampoos, shower gels and bubble baths.

27. The composition according to claim 13, wherein the composition is in a form chosen from rinse-out and leave-in conditioner compositions; compositions for permanent-waving, straightening, dyeing and bleaching; compositions to be applied before dyeing, bleaching, permanent-waving and straightening; compositions to be applied after dyeing, bleaching, permanent-waving and straightening; and compositions to be applied between the two steps of a permanent-waving and straightening operation.

28. A pearlescent composition produced by combining
an aqueous medium,
at least one conditioning agent,
at least one surfactant and
at least one agent chosen from cyclodextrins,
wherein said at least one surfactant and said at least one agent chosen from cyclodextrins form at least one soluble complex sufficient to pearl the composition, and
wherein the at least one conditioning agent is chosen from poly-α-olefins, fluorinated oils, fluorinated waxes, fluorinated gums, carboxylic acid esters, silicones, cationic polymers, mineral oils, plant oils, animal oils, ceramides, and pseudoceramides.

* * * * *